US00PP36737P2

(12) United States Plant Patent
Mukundan

(10) Patent No.: US PP36,737 P2
(45) Date of Patent: Jun. 10, 2025

(54) ***PHILODENDRON* PLANT NAMED 'MUKCHOC'**

(50) Latin Name: *Philodendron hybrida*
Varietal Denomination: MUKCHOC

(71) Applicant: Parthasarathy Mukundan, Tamil Nadu (IN)

(72) Inventor: Parthasarathy Mukundan, Tamil Nadu (IN)

( * ) Notice: Subject to any disclaimer, the term of this patent is extended or adjusted under 35 U.S.C. 154(b) by 0 days.

(21) Appl. No.: 18/542,729

(22) Filed: Dec. 17, 2023

(51) Int. Cl.
*A01H 5/12* (2018.01)
*A01H 6/10* (2018.01)

(52) U.S. Cl.
USPC ..... Plt./381

(58) Field of Classification Search
USPC ..... Plt./381
CPC ..... A01H 5/12; A01H 5/00; A01H 6/10
See application file for complete search history.

(56) References Cited

U.S. PATENT DOCUMENTS

PP14,116 P3 * 8/2003 Osiecki ..... A01H 6/10 Plt./381

* cited by examiner

*Primary Examiner* — June Hwu
(74) *Attorney, Agent, or Firm* — C. Anne Whealy

(57) ABSTRACT

A new and distinct cultivar of *Philodendron* plant named 'MUKCHOC', characterized by its mostly upright to outwardly spreading to arching plant habit; vigorous and robust growth habit; closely-stacked leaves impart a relatively compact, dense, full and symmetrical plant form; glossy leaves that vary in color with development and light levels; leaves that may be brown, greenish brown, reddish green, green and/or reddish bronze in color with contrasting venation; and glossy leaf petioles that are reddish brown to brown in color.

2 Drawing Sheets

Figure 1:
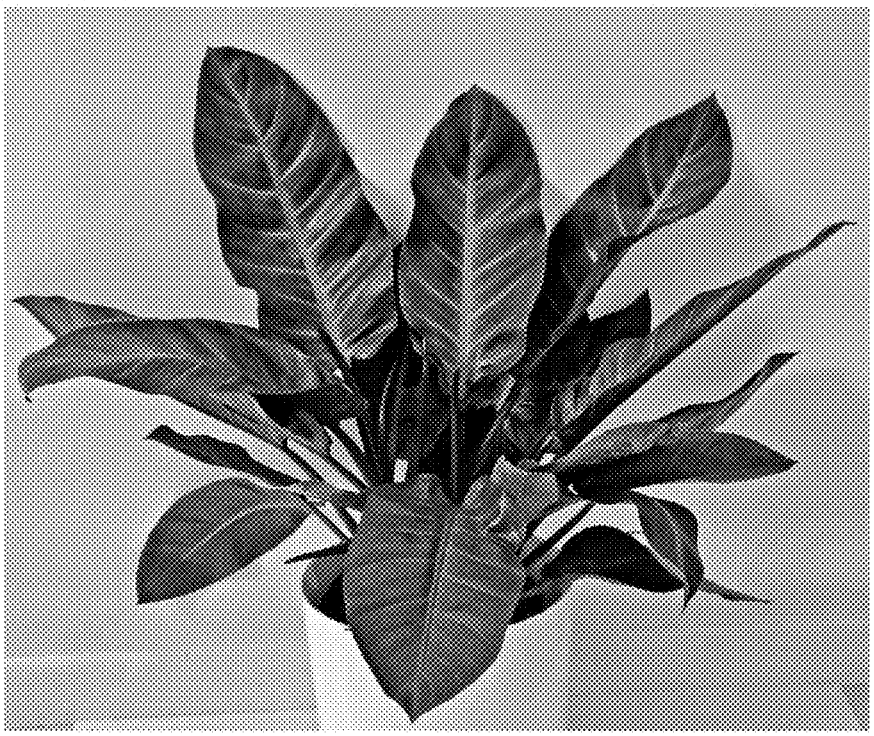

Botanical designation: *Philodendron hybrida.*
Cultivar denomination: 'MUKCHOC'.

STATEMENT REGARDING PRIOR DISCLOSURES BY INVENTOR/APPLICANT

An European Community Plant Breeder's Rights application for the instant plant was filed by the Inventor/Applicant and his company, K.S.G.'s Farm & Nursery on May 17, 2022, application number 2022/1242. Foreign priority is not claimed to this application.

The Inventor/Applicant assert that no sales, offers for sale or public distribution of the instant plant occurred more than one year prior to the effective filing date of this application.

Any information about the claimed plant would have been obtained from a direct or indirect disclosure from the Inventor/Applicant. Inventor/Applicant claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Philodendron* plant, botanically known as *Philodendron hybrida* and hereinafter referred to by the name 'MUKCHOC'.

The new *Philodendron* plant is the product of a controlled breeding program conducted by the Inventor in Bangalore, India. The objective of the breeding program is to create new compact, uniform and dense *Philodendron* plants with good plant vigor, interesting and unique leaf colors, resistance to pathogens and pests and tolerance to low temperatures.

The new *Philodendron* plant is the product of a cross-pollination conducted by the Inventor on Oct. 9, 2010 in Bangalore, India of *Philodendron hybrida* 'Black Cardinal', disclosed in U.S. Plant Pat. No. 5,355, as the female, or seed, parent with *Philodendron hybrida* 'Red Arrow', not patented, as the male, or pollen, parent. The new *Philodendron* plant was discovered and selected by the Inventor in September, 2011 as a single plant from within the resultant progeny of the stated cross-pollination in a controlled environment in Bangalore, India.

Asexual reproduction of the new *Philodendron* plant by cuttings in a controlled environment in Bangalore, Karnataka, India since April, 2012 has shown that the unique features of this new *Philodendron* plant are stable and reproduced true to type in successive generations of asexual reproduction.

SUMMARY OF THE INVENTION

Plants of the new *Philodendron* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MUKCHOC'. These characteristics in combination distinguish 'MUKCHOC' as a new and distinct *Philodendron* plant:

1. Mostly upright to outwardly spreading to arching plant habit.

2. Vigorous and robust growth habit.
3. Closely-stacked leaves impart a relatively compact, dense, full and symmetrical plant form.
4. Glossy leaves that vary in color with development and light levels; leaves may be brown, greenish brown, reddish green, green and/or reddish bronze in color with contrasting venation.
5. Glossy leaf petioles that are reddish brown to brown in color.

Plants of the new *Philodendron* differ primarily from plants of the female parent, 'Black Cardinal', in the following characteristics:

1. Leaves of plants of the new *Philodendron* are not as broad as leaves of plants of 'Black Cardinal'.
2. Leaves of plants of the new *Philodendron* can be brown, greenish brown, reddish green, green and/or reddish bronze in color whereas leaves of plants of 'Black Cardinal' are deep red to close to black in color.
3. Leaf petioles of plants of the new *Philodendron* are reddish brown to brown in color whereas leaf petioles of plants of 'Black Cardinal' are close to black in color.

Plants of the new *Philodendron* differ primarily from plants of the male parent, 'Red Arrow', in the following characteristics:

1. Plants of the new *Philodendron* are denser, more compact and more uniform than plants of 'Red Arrow'.
2. Leaves of plants of the new *Philodendron* are smaller than leaves of plants of 'Red Arrow'.
3. Leaves of plants of the new *Philodendron* can be brown, greenish brown, reddish green, green and/or reddish bronze in color whereas leaves of plants of 'Red Arrow' can be maroon red to dark brown and/or dull green in color.
4. Plants of the new *Philodendron* have stouter leaf petioles than plants of 'Red Arrow'.
5. Leaf petioles of plants of the new *Philodendron* are reddish brown to brown in color whereas leaf petioles of plants of 'Red Arrow' are close to maroon red in color.

Plants of the new *Philodendron* can be compared to plants of *Philodendron hybrida* 'Rojo Congo', disclosed in U.S. Plant Pat. No. 14,116. Plants of the new *Philodendron* differ from plants of 'Rojo Congo' in the following characteristics:

1. Plants of the new *Philodendron* are denser and more compact than plants of 'Rojo Congo'.
2. Leaves of plants of the new *Philodendron* are smaller than leaves of plants of 'Rojo Congo'.
3. Leaves of plants of the new *Philodendron* can be brown, greenish brown, reddish green, green and/or reddish bronze in color whereas leaves of plants of 'Rojo Congo' are maroon brown to dull dark green in color.
4. Plants of the new *Philodendron* have shorter and stouter leaf petioles than plants of 'Rojo Congo'.
5. Leaf petioles of plants of the new *Philodendron* are reddish brown to brown in color whereas leaf petioles of plants of 'Rojo Congo' are dark purple brown in color.

Plants of the new *Philodendron* can be compared to plants of *Philodendron hybrida* 'McColley's Finale', disclosed in U.S. Plant Pat. No. 12,144. Plants of the new *Philodendron* differ from plants of 'McColley's Finale' in the following characteristics:

1. Plants of the new *Philodendron* are larger, denser and more upright than plants of 'McColley's Finale'.
2. Leaves of plants of the new *Philodendron* are narrower and more erect than leaves of plants of 'McColley's Finale'.
3. Leaves of plants of the new *Philodendron* can be brown, greenish brown, reddish green, green and/or reddish bronze in color whereas leaves of plants of 'McColley's Finale' are dull chestnut red to medium green in color.
4. Leaf petioles of plants of the new *Philodendron* are reddish brown to brown in color whereas leaf petioles of plants of 'McColley's Finale' are reddish black in color.

BRIEF DESCRIPTION OF THE PHOTOGRAPHS

The accompanying photographs illustrate the overall appearance of the new *Philodendron* plant showing the colors as true as it is reasonably possible to obtain in colored reproductions of this type. Colors in the photographs may differ slightly from the color values cited in the detailed botanical description which accurately describe the colors of the new *Philodendron* plant.

The photograph on the first sheet (FIG. 1) is a side perspective view of a typical plant of 'MUKCHOC' grown in a container under 80% shade.

Figure 2:
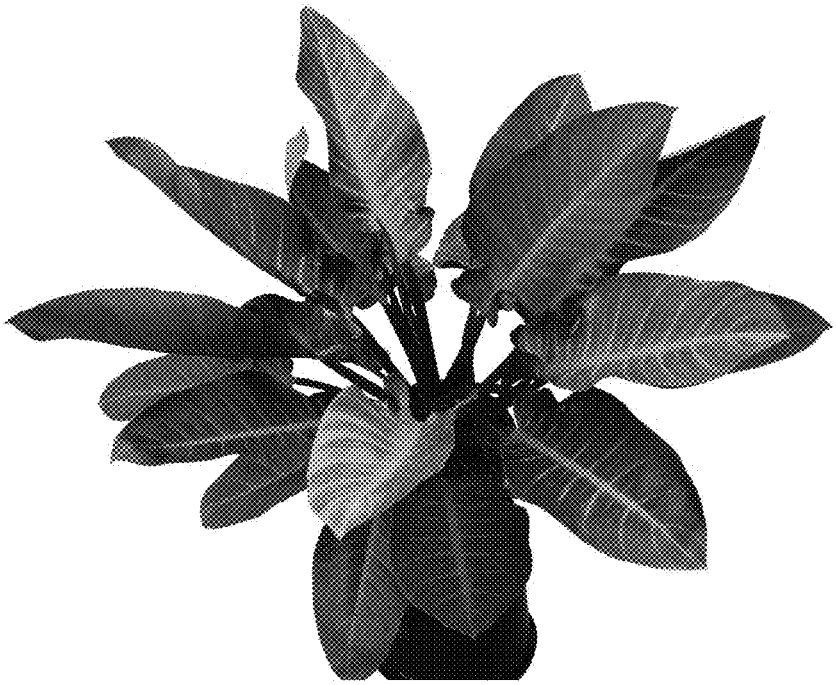

The photograph on the second sheet (FIG. 2) is a side perspective view of a typical plant of 'MUKCHOC' grown in a container under 30% shade. Plants used for the photographs were two years old.

DETAILED BOTANICAL DESCRIPTION

The following observations and measurements describe plants grown in 20-cm containers during the summer in shade houses providing 80% shade in Miami, Florida. Plants were grown under environmental conditions and cultural practices which approximate those generally used in commercial *Philodendron* production. During the production of the plants, day temperatures ranged from 25° C. to 32° C. and night temperatures ranged from 15° C. to 23° C. Plants were one year old when the detailed description was taken. In the following description, color references are made to The Royal Horticultural Society Colour Chart, 2015 Edition, except where general terms of ordinary dictionary significance are used.

Botanical classification: *Philodendron hybrida* 'MUKCHOC'.

Parentage:

*Female, or seed, parent.*—*Philodendron hybrida* 'Black Cardinal', disclosed in U.S. Plant Pat. No. 5,355.

*Male, or pollen, parent.*—*Philodendron hybrida* 'Red Arrow', not patented.

Propagation:

*Type.*—By cuttings.

*Time to initiate roots.*—About three weeks.

*Time to produce a rooted young plant.*—About six weeks.

*Root description.*—Fibrous, medium in thickness; typically white in color, actual color of the roots is dependent on substrate composition, water quality, fertilizers, substrate temperature and age of roots.

*Rooting habit.*—Moderately freely branching; medium density.

Plant description:

*Plant and growth habit*.—Mostly upright to outwardly spreading to arching plant habit; vigorous and robust growth habit; closely-stacked leaves impart a relatively compact, dense, full and symmetrical plant form.

*Plant height*.—About 55 cm.

*Plant diameter or spread*.—About 68 cm to 70 cm.

*Stem description*.—Branching habit: Plants of the new *Philodendron* typically have a single basal shoot; pinching will induce lateral branching. Length: About 2.5 cm. Diameter: About 2.6 cm. Internode length: About 1 cm. Aspect: Mostly upright. Strength: Strong. Texture and luster: Smooth, glabrous; matte. Color: Close to 177A.

Leaf description:

*Arrangement*.—Alternate; simple.

*Length*.—About 24 cm.

*Width*.—About 9.5 cm to 9.75 cm.

*Shape*.—Long elliptic to broadly lanceolate.

*Apex*.—Acuminate.

*Base*.—Narrowly obtuse.

*Margin*.—Entire; slightly and coarsely undulate; proximally, irregularly indented and puckered.

*Texture and luster, upper and lower surfaces*.—Smooth, glabrous; glossy.

*Venation pattern*.—Pinnate.

*Color*.—Developing leaves, upper surface: Close to 166A, 178A or close to 148A variably overlain with close to 178A. Developing leaves, lower surface: Close to 166A or close to 148A variably overlain with close to 166A. Fully expanded leaves, upper surface: Close to 178A, 147A or 148A; venation, close to N148A variably overlain with close to 178A or 166A to 166B. Fully expanded leaves, lower surface: Close to 166A, 147A to 147B, or 148A to 148B; venation, close to N148B variably overlain with close to 166A to 166B.

*Petioles*.—Length: About 14.5 cm. Diameter: About 5 mm by 9 mm. Aspect: Initially erect and then outwardly arching. Strength: Strong; flexible. Texture and luster, upper and lower surfaces: Smooth, glabrous; glossy. Color, upper and lower surfaces: Close to 166A, 177A and/or 178A.

Inflorescence description: To date, inflorescence initiation and development has not been observed on plants of the new *Philodendron*.

Pathogen & pest resistance: To date, plants of the new *Philodendron* not been observed to be resistant to pathogens and pests common to *Philodendron* plants.

Temperature tolerance: Plants of the new *Philodendron* have been observed to tolerate temperatures ranging from about 8 C to about 40 C and to be suitable for USDA Hardiness Zones 11 to 13.

It is claimed:

1. A new and distinct *Philodendron* plant named 'MUKCHOC' as herein illustrated and described.

* * * * *